(12) United States Patent
Gordon et al.

(10) Patent No.: US 7,638,645 B2
(45) Date of Patent: Dec. 29, 2009

(54) METAL (IV) TETRA-AMIDINATE COMPOUNDS AND THEIR USE IN VAPOR DEPOSITION

(75) Inventors: Roy G. Gordon, Cambridge, MA (US); Jean-Sebastien Lehn, Watertown, MA (US); Huazhi Li, Somerville, MA (US)

(73) Assignee: President and Fellows of Harvard University, Cambridge, MA (US)

( * ) Notice: Subject to any disclaimer, the term of this patent is extended or adjusted under 35 U.S.C. 154(b) by 556 days.

(21) Appl. No.: 11/581,987

(22) Filed: Oct. 17, 2006

(65) Prior Publication Data
US 2008/0003359 A1 Jan. 3, 2008

Related U.S. Application Data

(60) Provisional application No. 60/817,209, filed on Jun. 28, 2006.

(51) Int. Cl.
C07F 7/00 (2006.01)
C07F 15/00 (2006.01)
C07F 11/00 (2006.01)
C07F 5/00 (2006.01)
C23C 16/00 (2006.01)

(52) U.S. Cl. .................... 556/51; 556/42; 556/45; 556/57; 556/137; 534/11; 534/15; 427/248.1

(58) Field of Classification Search ............ 556/42, 556/45, 51, 57, 137; 534/11, 15; 427/248.1
See application file for complete search history.

(56) References Cited

U.S. PATENT DOCUMENTS 7,002,033 B1 * 2/2006 Sakai et al. .......... 556/137

FOREIGN PATENT DOCUMENTS

| WO | WO-91/08322 | 6/1991 |
| WO | WO-2004/046417 A2 | 6/2004 |
| WO | WO-2004/046417 A3 | 6/2004 |

OTHER PUBLICATIONS

Fix, et al., "Chemical Vapor Deposition of Titanium, Zirconium, and Hafnium Nitride Thin Films", American Chemical Society, vol. 3(6), pp. 1138-1148, 1991.
International Search Report from PCT/US2007/014768, mailed Nov. 11, 2007.

* cited by examiner

*Primary Examiner*—Porfirio Nazario Gonzalez
(74) *Attorney, Agent, or Firm*—WilmerHale LLP

(57) ABSTRACT

Metal(IV) tetrakis(N,N'-dialkylamidinates) were synthesized and characterized. Exemplary metals include hafnium, zirconium, tantalum, niobium, tungsten, molybdenum, tin and uranium. These compounds are volatile, highly stable thermally, and suitable for vapor deposition of metals and their oxides, nitrides and other compounds.

31 Claims, 3 Drawing Sheets

METAL (IV) TETRA-AMIDINATE COMPOUNDS AND THEIR USE IN VAPOR DEPOSITION

CROSS-REFERENCE TO RELATED APPLICATION

This application claims the benefit under 35 U.S.C. §119 (e) of U.S. Provisional Patent Application No. 60/817,209 filed on Jun. 28, 2006, entitled Metal(IV) Tetra-Amidinate Compounds And Their Use In Vapor Deposition, which is incorporated herein by reference in its entirety.

BACKGROUND OF THE INVENTION

1. Field of the Invention

This invention relates to novel compounds containing metals in the +4 oxidation state bonded to four amidinate ligands. This invention also relates to the use of these compounds as precursors for vapor deposition of metal-containing layers.

2. Description of the Related Art

Electrically insulating materials with high dielectric constants ("high-k dielectrics") are now being used in the manufacture of computer memories (dynamic random access memories, or DRAMs). Aluminum oxide and tantalum oxide are currently in commercial use in DRAMs, and oxides, nitrides and silicates of hafnium and zirconium are being tested as alternatives for future use. These high-k materials may also be used as insulators in future transistors in microelectronic devices.

Electrically conductive nitrides of metals such as tantalum, tungsten, hafnium, zirconium, titanium, niobium and molybdenum have a variety of applications and potential applications, such as barriers against the diffusion of copper, and as electrodes for capacitors and transistors in microelectronic devices. These refractory metals also find use as adhesion-promoting layers for copper, and as electrodes or electrical interconnections.

Vapor deposition is a preferred method for making these materials. Vapor deposition is a generic term that comprises chemical vapor deposition (CVD) and atomic layer deposition (ALD). In a CVD process, one or more vapors are delivered to a surface on which solid material is deposited; the chemical reactions that convert the vapor to a solid are initiated by means such as heat, light or electrical excitation (plasma activation). In an ALD process, two or more vapors are delivered alternately to the surface on which reactions take place to deposit a solid product. ALD is capable of depositing these materials inside the very narrow structures in modern DRAMs. CVD generally provides higher deposition rates than ALD, but with less uniform deposition inside very narrow holes.

Successful precursors for vapor deposition must be volatile, thermally stable, and highly reactive. Identifying compounds that meet all of these challenging requirements is difficult. Fully satisfactory precursors for metals such as hafnium, zirconium, tantalum, niobium, tungsten, molybdenum, tin, tellurium and uranium are not known. Halides, such as $ZrCl_4$, $HfCl_4$, and $TaCl_5$, have difficulty nucleating on some substrate surfaces, and the byproduct hydrochloric acid prevents fully conformal deposition inside narrow holes. Alkoxides and dialkylamides have less than optimal thermal stabilities. Organometallic compounds may lack suitable reactivity, leaving carbon as an impurity in the films. Thus there is a need for more volatile, thermally stable, and highly reactive sources for these metals.

SUMMARY OF THE INVENTION

One aspect of the invention includes novel compounds containing metals in the +4 oxidation state bonded to four amidinate ligands. In preferred embodiments, these ligands comprise N,N'-dialkylamidinate ligands. Preferred metals include hafnium, zirconium, tantalum, niobium, tungsten, molybdenum, tin, tellurium and uranium.

In one or more embodiments, the compound has the structural formula

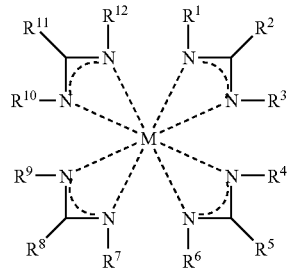

in which M is a metal in the +4 oxidation state and each of $R^1$ through $R^{12}$ are independently selected from the group consisting of hydrogen, hydrocarbon groups, substituted hydrocarbon groups, and other groups of non-metallic atoms.

In one or more embodiments, the hydrocarbon group is selected from the group consisting of alkyl, cycloalkyl, alkenyl, cycloalkenyl, alkynyl and cycloalkynyl groups and the substituted hydrocarbon group consisting of fluoride derivatives of hydrocarbons, or the group comprising non-metallic atoms are selected from the group consisting of alkylsilyl and alkyl amino groups.

In one or more embodiments, the metal M is selected from the group consisting of zirconium, hafnium, tin, tantalum, niobium, tungsten, molybdenum, uranium, rhenium, platinum, osmium, iridium, ruthenium, palladium, titanium, rhodium, vanadium, cerium and lead, or the metal M is selected from the group consisting of hafnium, zirconium, tantalum, niobium, tungsten, molybdenum, tin, tellurium and uranium.

In one or more embodiments, at least one of $R^1$ through $R^{12}$ is a lower alkyl having 5 or less carbons.

In one or more embodiments, $R^1$ through $R^{12}$ is selected from the group consisting of lower alkyls having 5 or less carbons and hydrogen.

In one or more embodiments, $R^1$, $R^3$, $R^4$, $R^6$, $R^7$, $R^9$, $R^{10}$ and $R^{12}$ are alkyl groups that are un-branched at the α-position.

Another aspect of the present invention includes a process for depositing films comprising metals using the novel compounds according to one or more embodiments of the invention. The process includes exposing a heated surface to the vapor of one or more volatile metal tetra-amidinate compounds. Exemplary deposition methods include Chemical Vapor Deposition (CVD) and Atomic Layer Deposition (ALD).

In one or more embodiments, the process includes exposing the substrate to a source of oxygen, and the thin film comprises a metal oxide.

In one or more embodiments, the source of oxygen comprises water vapor, or dioxygen, or ozone.

In one or more embodiments, the process includes exposing the substrate to a source of nitrogen, and the thin film comprises a metal nitride.

In one or more embodiments, the source of nitrogen comprises ammonia.

In one or more embodiments, the vapor is obtained by vaporizing a solid metal tetra-amidinate compound, or by vaporizing a liquid metal tetra-amidinate compound.

In one or more embodiments, the vapor is obtained by vaporizing a metal tetra-amidinate at a temperature in the range of 100 to 250° C.

In one or more embodiments, the surface is at a temperature in the range of about 200 to 500° C.

BRIEF DESCRIPTION OF THE DRAWINGS

The foregoing and various other aspects, features, and advantages of the present invention, as well as the invention itself, may be more fully appreciated with reference to the following detailed description of the invention when considered in connection with the following drawings. The drawings are presented for the purpose of illustration only and are not intended to be limiting of the invention, in which.

DETAILED DESCRIPTION OF THE INVENTION

Figure 1:
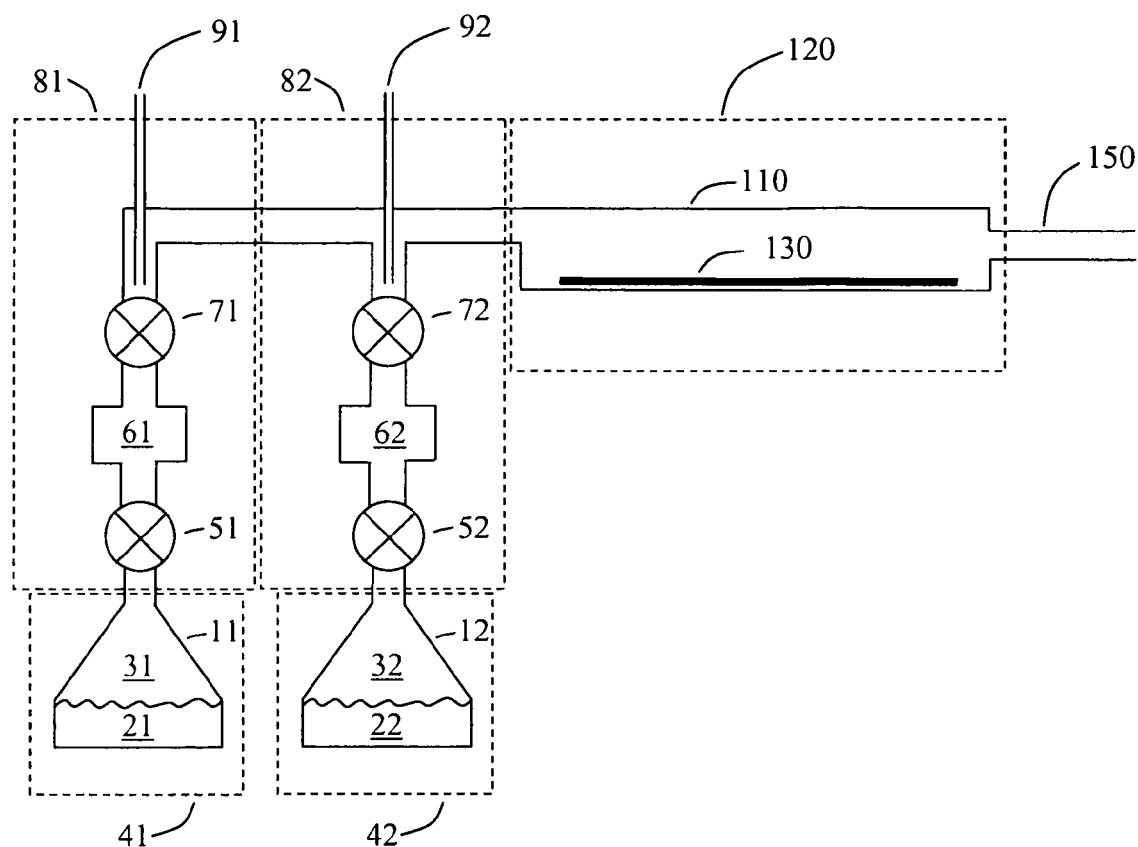
FIG. 1 is a schematic cross-sectional drawing of an ALD apparatus that can be used in some embodiments of the invention.

The present invention provides thermally stable, volatile metal compounds that are suitable for use in vapor deposition processes, including chemical vapor deposition and atomic layer deposition.

Preferred compounds include volatile metal(IV) tetrakis (N,N'-dialkylamidinates) complexes. Typically, these compounds are described by a monomeric formula 1,

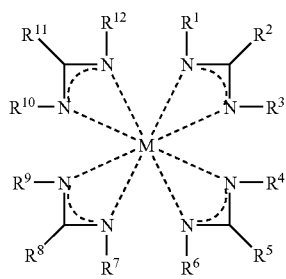

1 in which M is a metal in the +4 oxidation state and $R^1$ through $R^{12}$, e.g., $R''$, where n=1-12, may be independently chosen from hydrogen, hydrocarbon groups such as alkyl, cycloalkyl, alkenyl, cycloalkenyl, alkynyl and cycloalkynyl groups and fluoride derivatives thereof, or other groups comprising non-metallic atoms such as alkylsilyl and alkyl amino groups. Reference to $R''$ applies equally to each of $R^1$ through $R^{12}$, unless otherwise specified.

In one or more embodiments, $R''$ are lower alkyl groups containing 5 or less carbons. In one or more embodiments, $R''$ are a mixture of hydrogen and lower alkyl groups. In preferred embodiments $R''$ are chosen from the group comprising methyl, ethyl and n-propyl. These small alkyl groups are preferred because they are small enough to fit into the structure 1 with very stable chelate binding. In one or more embodiments, one or more of $R^1$, $R^3$, $R^4$, $R^6$, $R^7$, $R^9$, $R^{10}$ or $R^{12}$ are hydrocarbon groups lacking a branched α-carbon. As used herein, an α-carbon is a carbon bound directly to one nitrogen of an amidinate ligand. Alkyl groups that branch at the α-carbon, such as isopropyl, sec-butyl or tert-butyl, are less preferred because they are likely to cause too much crowding to fit into structure 1. Thus the branched alkyl groups will generally provide less stable metal amidinates. Nonetheless, branched groups are contemplated according to one or more embodiments, in particular, where a larger metal center is used or the branching occurs beyond the α-carbon.

Exemplary tetravalent metals that may be used in one or more embodiments of the invention include zirconium, hafnium, tin, tantalum, niobium, tungsten, molybdenum, uranium, rhenium, platinum, osmium, iridium, ruthenium, palladium, titanium, rhodium, vanadium, cerium, tellurium and lead. Tetravalent metal ions having relatively larger ionic radii form tetra-amidinate complexes that are particularly stable; those metals include zirconium, hafnium, tin, tantalum, niobium, tungsten, molybdenum, tellurium and uranium. Tetravalent metal ions having relatively smaller ionic radii that form tetra-amidinate include rhenium, platinum, osmium, iridium, ruthenium, palladium, titanium, rhodium and vanadium.

In one or more embodiments, the amidinate ligand is symmetric, e.g., the N-bound R groups such as $R^1$ and $R^3$ or $R^4$ and $R^6$, etc., are the same in formula 1. In one or more embodiments, the amidinate ligand is asymmetric, e.g., $R^1$ and $R^3$ are different in formula 1. In either embodiment, the carbon-bound R group, e.g., $R^2$ in formula 1, can be the same or different.

In one or more embodiments, metal tetrakis(N,N'-dialkylamidinate) compounds are prepared using N,N'-dialkylamidines. Symmetric amidines may be formed by condensation of amines with nitriles catalyzed by lanthanum trifluoromethanesulfonate (also known as lanthanum triflate), $La(CF_3SO_3)_3$:

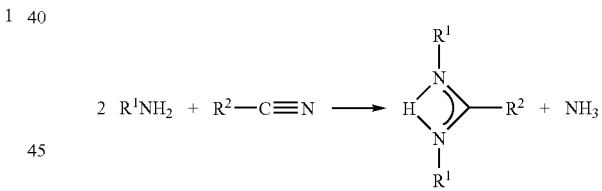

2

Amines in which $R^1$ is an alkyl group that is not branched at the α-position, such as n-propyl, n-butyl or isobutyl, react within a few hours to a few days at reflux temperature. Amines in which $R^1$ is a methyl or ethyl group are so volatile that they must be confined within a pressure vessel during the reaction. During the course of the reaction the byproduct ammonia may be released from the pressure vessel by a back-pressure regulator. Complete reaction takes a few days at room temperature, or shorter periods at higher temperatures and pressures. A less expensive catalyst for this reaction can be made from mixed triflates of the naturally-occurring mixture of lanthanum metals ("misch metal").

Unsymmetrical amidines can be prepared according to the following reactions:

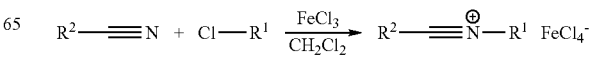

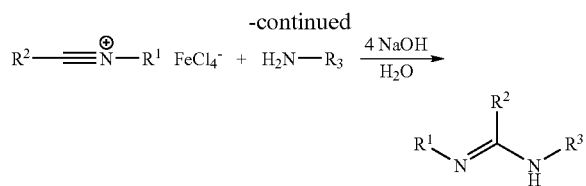

Metal amidinates can be prepared by exchange reactions in which a metal dialkylamide is reacted with an amidine. Alternately, the amidine can be converted to its alkali salt by reaction with butyllithium or with sodium amide or with potassium hydride. The alkali amidinate can then undergo a salt metathesis reaction with a metal chloride to form the metal amidinate. A more commonly-used method to form lithium amidinates is to react a carbodiimide with a lithium alkyl. This conventional synthetic route is more effective when the $R^1$ and $R^3$ alkyl groups are branched at the α-position, because the corresponding carbodiimides are more stable.

The metal tetra-amidinate compounds may be used to form metal-containing films in a vapor deposition process. Vapors of the compounds according to one or more embodiments may be used to deposit materials such as metals, metal oxides, metal nitrides, metal oxynitrides, metal sulfides and the like. These vapor deposition processes include CVD and ALD. In CVD, a vapor of the metal tetra-amidinate is supplied to the surface, optionally along with a co-reactant gas or vapor. In ALD, a vapor of the metal tetra-amidinate and a co-reactant are supplied to the surface in alternating time periods. CVD processing is described, for example, in U.S. Pat. No. 5,139,999, which is hereby incorporated by reference, and in the "Handbook of Chemical Vapor Deposition: Principles, Technology and Applications" by Hugh O. Pierson ($2^{nd}$ edition, Noyes Publications, 1999). ALD processing is described in U.S. Pat. No. 6,969,539, which is hereby incorporated by reference, and in the article "Atomic Layer Deposition" by M. Ritala and M. Leskela, vol. 1, p. 103 of the Handbook of Thin Film Materials (Ed. H. Nalwa, Academic Press, 2002). Oxides may be formed using co-reactants such as water vapor, dioxygen, ozone, hydrogen peroxide and alcohols or a plasma formed from an oxygen-containing gas or vapor. Nitrides may be formed using co-reactants such as ammonia, a hydrazine or a plasma formed from a nitrogen-containing gas or vapor. Sulfides may be formed using co-reactants such as hydrogen sulfide or a plasma formed from a sulfur-containing gas or vapor.

An apparatus for carrying out ALD is shown schematically in cross-section in FIG. 1. During operation of the ALD process, carrier gas, such as nitrogen, flows continuously from sources 91 and 92 through the deposition chamber 110 into pipe 150 to a trap and vacuum pump. A tetra-amidinate precursor 21 is held in vessel 11 that is heated in oven 41 to a temperature sufficient to form its vapor 31. Vapor 31 of the tetravalent amidinate precursor flows into evacuated chamber 61 in oven 81 when valve 51 is opened. Valve 51 is then closed and valve 71 opened to allow an aliquot of precursor vapor to flow over the substrate 130 inside heated furnace 120. Valve 71 is then closed and time is allowed for excess unreacted precursor to be purged from chamber 110 along with volatile reaction byproducts. The second reagent 22, such as water or ammonia, is placed in vessel 12, usually kept at room temperature. Vapor 32 of the second reagent is allowed to flow into vapor space 62 by opening valve 52, which is then closed. Valve 72 is opened to allow an aliquot of the second reagent to flow into the deposition chamber 110. Valve 72 is then closed and time is allowed for unreacted excess of the second reagent to be purged from the deposition chamber 110 along with volatile reaction byproducts. This cycle of operations is then repeated to build up the desired thickness of coating on substrate 130.

An apparatus for carrying out CVD includes many similar features. The apparatus may include a vessel housing a tetra-amidinate precursor that is heated to a temperature to form its vapor. The tetra-amidinate precursor vapor flows from the vessel and into a heated furnace housing the substrate. Additional co-reactant vapors may be introduced into the heated furnace with the tetra-amidinate precursor, or the co-reactant vapors may be premixed with the tetra-amidinate vapor prior to their exposure to the heated substrate. An exhaust system removes byproducts and unreacted reactants from the furnace.

The tetra-amidinate precursor may be used as a neat liquid, in solution in the appropriate solvent, or as a solid. Suitable deposition conditions, such as temperatures for vaporization and deposition, pressures, flow rates, and co-reactants may be readily determined by one of skill in the art. Exemplary ALD and CVD conditions include substrate temperatures of 200 to 500° C., and more preferably 300 to 400° C., vapor pressures in the range of 0.1 to 10 Torr, and more preferably 1 to 5 Torr, vaporization temperatures of about 100 to 250° C., and more preferably 150 to 200° C., ALD doses of 1 to 100 nmol cm$^{-2}$ of deposited surface, and more preferably 2 to 20 nmol cm$^{-2}$, and ALD exposures of 0.01 Torr-sec to 10 Torr-sec, and more preferably 0.1 to 1 Torr-sec. The ALD exposures needed to cover features with high aspect ratios increase approximately as the square of the aspect ratio.

EXAMPLES

Example 1

Synthesis of N,N'-di-iso-butylacetamidine

A solution of iso-butylamine (7.3 g, 0.1 mol), acetonitrile (4.1 g, 0.1 mol) and lanthanum triflate, La(CF$_3$SO$_3$)$_3$, (1.2 g, 0.002 mol) was refluxed for 30 hr under nitrogen atmosphere. The unreacted starting material and byproduct 2,4,6-trimethyl-1,3,5-triazine were removed by fractional distillation at 40° C. at around 0.2 Torr. Then the colorless N,N'-di-iso-butylacetamidine was distilled at 95° C. and 0.06 torr. Further purification was done by a second distillation. Yield: 6.4 g (75% based on iso-butylamine). $^1$H NMR (benzene-d$_6$+a small amount of CD$_3$OD, ppm): 3.1 (d, 4, NCH$_2$), 1.9 (m, 2, CH(CH$_3$)$_2$), 1.7 (s, 3, CCH$_3$), 1.0 (d, 12, CH(CH$_3$)$_2$).

Example 2

Synthesis of tetrakis(N,N'-di-iso-butylacetamidinato) zirconium(IV), Zr($^i$Bu-AMD)$_4$ 0.8 g (3 mmol) of tetrakis(dimethylamido)zirconium(IV), Zr(NMe$_2$)$_4$, was dissolved in 10 ml of toluene and then cooled to −30° C. for 30 minutes. To this solution was added 2.3 g (13.5 mmol) N,N'-di-iso-butylacetamidine, $^i$Bu-AMD, and the mixture was heated at 90° C. overnight (ligand exchange reaction). After cooling to −30° C., a colorless crystalline material precipitated and was filtered out. Yield: 1.85 g (80%). $^1$H NMR (benzene-d$_6$, ppm): 3.10 (d, 16, J=6.9 Hz, NCH$_2$), 1.89 (m, 8, CH(CH$_3$)$_2$), 1.71 (s, 12, CCH$_3$), 1.00 (d, 48, J=6.6 Hz, d, CH(CH$_3$)$_2$). $^{13}$C NMR (benzene-d$_6$, ppm):

174 (CCH$_3$), 55.76 (NCH$_2$), 31.74 (CH(CH$_3$)$_2$), 21.134 (CH(CH$_3$)$_2$), 12.10 (CCH$_3$). Anal. Calcd. for C$_{40}$H$_{84}$N$_8$Zr: C, 62.53; H, 11.02; N, 14.58. Found: C, 62.76; H, 11.25; N, 14.50.

Figure 2:
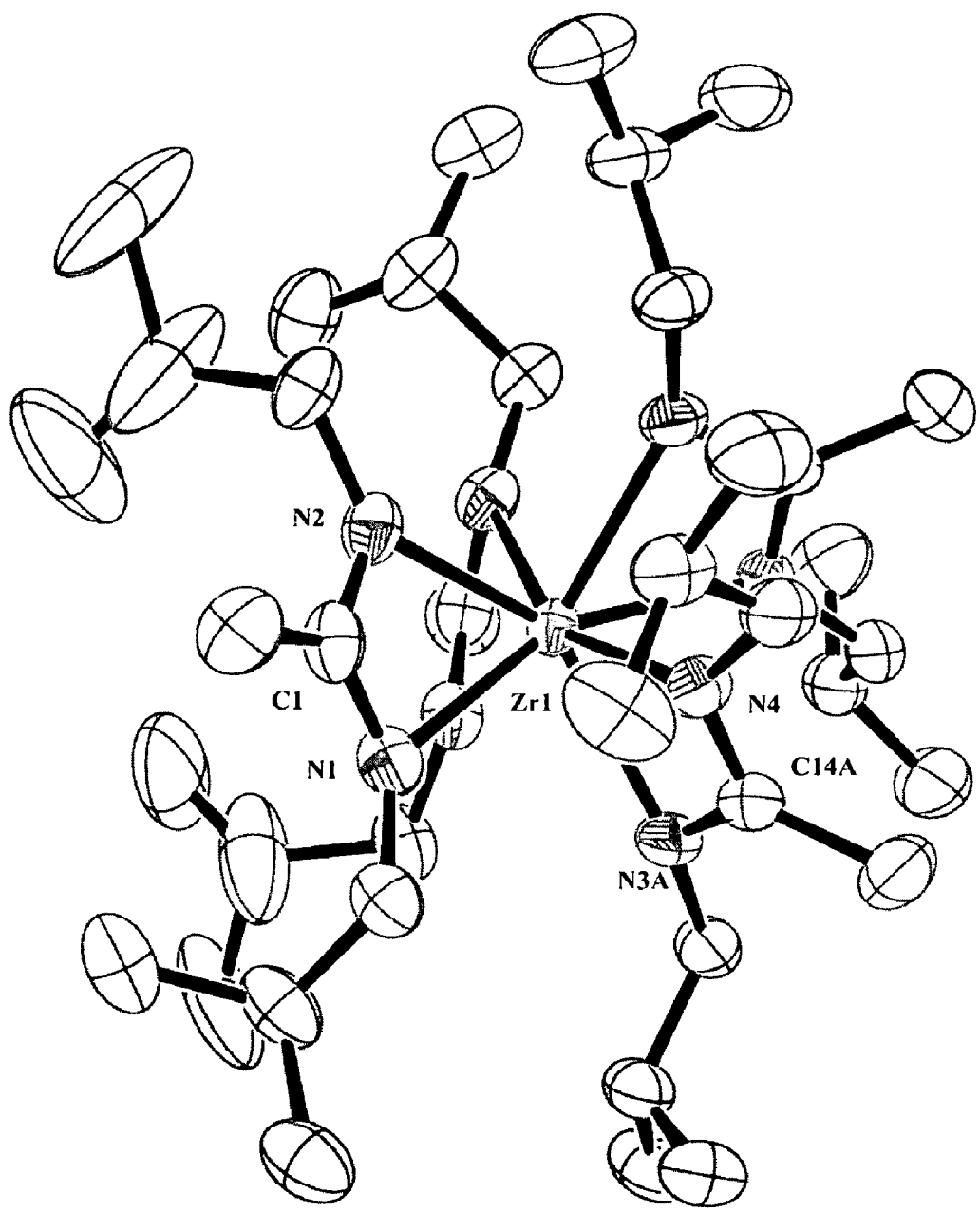
FIG. 2 is a drawing of the molecular structure of tetrakis (N,N'-di-iso-butylacetamidinato) zirconium(IV)

X-ray crystallography was used to determine the molecular structure of tetrakis(N,N'-di-iso-butylacetamidinato)zirconium(IV) shown in FIG. 2, where the atoms are represented by 50% thermal ellipsoids and hydrogen atoms are omitted for clarity. Each molecule contains one zirconium atom surrounded by 8 nitrogen atoms from the four amidinate ligands.

The temperature at which half of the product evaporated during thermogravimetric analysis (TG), $T_{1/2}$, is 240° C., measured in flowing nitrogen gas at atmospheric pressure. This TG experiment also demonstrated that the compound has a high thermal stability and completely vaporizes with negligible residue.

Example 3

Synthesis of tetrakis(N,N'-di-iso-butylacetamidinato) hafnium(IV), Hf($^i$Bu-AMD)$_4$ This compound was prepared in a way similar to that described in Example 2 for Zr($^i$Bu-AMD)$_4$, starting from 3 mmol of tetrakis(dimethylamido)hafnium(IV), Hf(NMe$_2$)$_4$. The product was isolated as a white powder. Yield: 2.17 g (85%). $^1$H NMR (benzene-d$_6$, ppm): 3.15 (d, 16, J=7.2 Hz, NCH$_2$), 1.87 (m, 8, CH(CH$_3$)$_2$), 1.70 (s, 12, CCH$_3$), 0.99 (d, 48, J=6.8 Hz, CH(CH$_3$)$_2$). Anal. Calcd. for C$_{40}$H$_{84}$HfN$_8$: C, 56.15; H, 9.90; N, 13.10. Found: 55.85; H, 9.77; N, 13.30.

The TG properties of this hafnium complex are similar to those of the zirconium complex described in Example 2.

Example 4

Synthesis of N,N'-dimethylacetamidine and its Lithium Salt

Anhydrous lanthanum triflate (3.00 g, 5.12 mmol) was placed into a pressure vessel. Dry acetonitrile (23.3 g, 0.568 mol) was condensed into the cold vessel. The vessel was cooled with liquid nitrogen and dry methylamine (53.1 g, 1.71 mol) was added. The vessel was sealed and allowed to warm to room temperature. Byproduct ammonia gas was released daily. Reaction was mostly complete after 3 days. Then the colorless N,N'-dimethylacetamidine was isolated by removing the byproduct N-methylacetamidine by sublimation at 20° C. and 0.04 torr. $^1$H NMR (benzene-d$_6$, ppm): 2.60 (s, 6, NCH$_3$), 1.40 (s, 3, CCH$_3$).

The lithium salt of N,N'-dimethylacetamidine was prepared by dissolving one volume of N,N'-dimethylacetamidine in 5 volumes of dry ether and cooling the solution to −78° C. An equal molar amount of butyllithium dissolved in hexanes was added slowly while stirring. The reaction mixture was allowed to warm to room temperature. The ether and pentane were removed under reduced pressure. Then the white solid residue was dissolved in dry dioxane. The resulting solution of N,N'-dimethylacetamidinato-lithium in dioxane was used in some of the following examples.

Example 5

Synthesis of tetrakis(N,N'-dimethylacetamidinato) zirconium(IV)

This compound was prepared by ligand exchange in a way similar to that described in Example 2 for Zr($^i$Bu-AMD)$_4$, using N,N'-dimethylacetamidine in place of N,N'-di-iso-butylacetamidine. Alternatively, ZrCl$_4$ was reacted with the lithium salt of N,N'-dimethylacetamidine dissolved in dioxane (salt metathesis reaction). This reaction mixture was heated to reflux for 8 hours. After evaporation of the dioxane, the solid residue was extracted with pentane. After decantation of the suspension to remove the precipitated lithium chloride, the pentane was evaporated under reduced pressure to yield the crude product, which was then purified by sublimation at 60° C. and a pressure of 40 mbar. It can also be sublimed at atmospheric pressure at 160° C. The yield was 24% after sublimation, when the synthesis was done on a small scale. $^1$H NMR (benzene-d$_6$, ppm); 3.03 (s, 24, NCH$_3$), 1.57 (s, 12, CCH$_3$). $^{13}$C NMR (benzene-d$_6$, ppm): 175.99 (s, CCH$_3$), 34.55 (s, NCH$_3$), 9.84 (s, CCH$_3$). Anal. Calcd. for C$_{16}$H$_{36}$N$_8$Zr: C, 44.51; H, 8.40; N, 25.95. Found: C, 45.31; H, 7.92; N, 25.60; or, in a second analysis, C, 43.30; H, 8.76; N, 24.87. This product is more volatile than tetrakis(N,N'-di-iso-butylacetamidinato)zirconium(IV), the product of Example 2 because its $T_{1/2}$ value from the TG curve is 216° C. with 0.6% residue. Its melting point is about 168° C.

Example 6

Synthesis of tetrakis(N,N'-dimethylacetamidinato) hafnium(IV)

This compound was prepared from HfCl$_4$ by the salt metathesis reaction described in Example 5. $^1$H NMR (benzene-d$_6$, ppm); 3.07 (s, 24, NCH$_3$), 1.55 (s, 12, CCH$_3$). $^{13}$C NMR (benzene-d$_6$, ppm); 175.69 (s, CCH$_3$), 34.31 (s, NCH$_3$), 10.09 (s, CCH$_3$). Anal. Calcd. for C$_{16}$H$_{36}$HfN$_8$: C, 37.03; H, 6.99; N, 21.59. Found: 37.00; H, 6.89; N, 21.34. This product is more volatile than tetrakis(N,N'-di-iso-butylacetamidinato) hafnium(IV), the product of Example 3 because its $T_{1/2}$ value from the TG curve is 221° C. Its residue after evaporation is negligible, less than 1%, and its melting point is about 171° C.

Example 7

Synthesis of tetrakis(N,N'-dimethylpropionamidinato)zirconium(IV)

A dioxane solution of lithium N,N'-dimethylpropionamidinate was prepared by the method described in Example 4, using propionitrile in place of acetonitrile. This solution was then used with ZrCl$_4$ in the salt metathesis method described in Example 5 to prepare tetrakis(N,N'-dimethylpropionamidinato)zirconium(IV). This compound may also be prepared by a ligand exchange reaction similar to the one described in Example 2. $^1$H NMR (benzene-d$_6$, ppm); 3.07 (s, 24, NCH$_3$), 2.10 (q, 8, J=7.6 Hz, CH$_2$CH$_3$), 0.96 (t, 12, J=7.6 Hz, CH$_2$CH$_3$). $^{13}$C NMR (benzene-d$_6$, ppm); 180.12 (s, CCH$_2$CH$_3$), 33.92 (s, NCH$_3$), 17.31 (s, CCH$_2$CH$_3$), 10.41 (s, CCH$_2$CH$_3$). Anal. Calcd. for C$_{20}$H$_{44}$N$_8$Zr: C, 49.24; H, 9.09; N, 22.97. Found: 49.42; H, 9.04; N, 22.43. Its melting point is 109° C., which is low enough so that it is a liquid at a temperature high enough to vaporize it in a bubbler. Its $T_{1/2}$ value from the TG curve is 245° C. with a negligible residue of 0.6%.

Example 8

Synthesis of tetrakis(N,N'-dimethylpropionamidinato)hafnium(IV)

Figure 3:
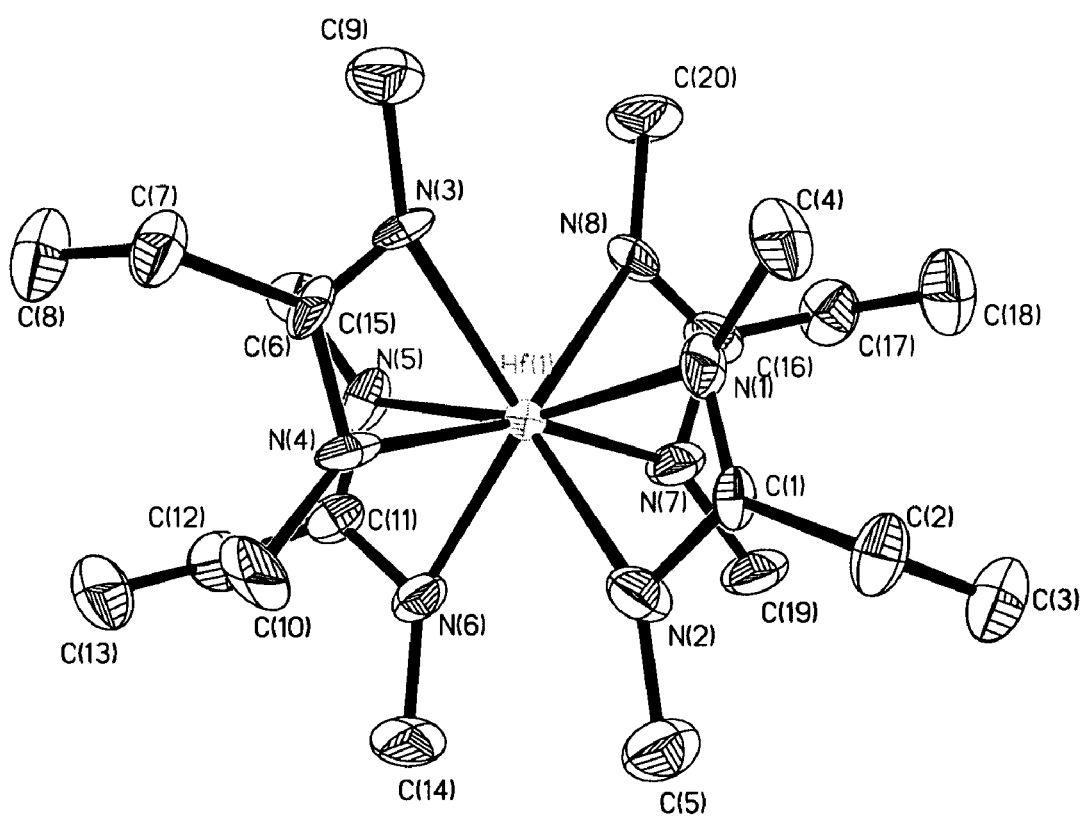
FIG. 3 is a drawing of the molecular structure of tetrakis (N,N'-dimethylpropionamidinato) hafnium(IV).

This compound was prepared from HfCl$_4$ by the salt metathesis reaction described in Example 7. It may also be prepared by a ligand exchange reaction similar to the one described in Example 1. $^1$H NMR (benzene-$d_6$, ppm): 3.10 (s, 24, NCH$_3$), 2.08 (q, 8, J=7.6 Hz, CH$_2$CH$_3$), 0.95 (t, 12, J=7.6 Hz, CH$_2$CH$_3$). $^{13}$C NMR (benzene-$d_6$, ppm): 179.75 (s, CCH$_2$CH$_3$), 33.71 (s, NCH$_3$), 17.51 (s, CCH$_2$CH$_3$), 10.40 (s, CCH$_2$CH$_3$). Anal. Calcd. for C$_{20}$H$_{44}$HfN$_8$: C, 41.77; H, 7.71; N, 19.48. Found: 42.32; H, 8.11; N, 19.18. Its melting point is 114° C., which is low enough so that it is a liquid at a temperature high enough to vaporize it in a bubbler. Its T$_{1/2}$ value from the TG curve is 252° C., with a negligible non-volatile residue. X-ray crystallography was used to determine the molecular structure of tetrakis(N,N'-dimethylpropionamidinato)hafnium(IV) shown in FIG. 3, where the atoms are represented by 50% thermal ellipsoids and hydrogen atoms are omitted for clarity. Each molecule contains one hafnium atom surrounded by 8 nitrogen atoms from the four amidinate ligands.

Example 9

Synthesis of tetrakis(N,N'-dimethylbutyramidinato) zirconium(IV)

A dioxane solution of lithium N,N'-dimethylbutyramidinate was prepared by the method described in Example 4, using butyronitrile in place of acetonitrile. This solution was then used with ZrCl$_4$ in the salt metathesis method described in Example 5 to prepare tetrakis(N,N'-dimethylbutyramidinato)zirconium(IV). This compound may also be prepared by a ligand exchange reaction similar to the one described in Example 1. The compound is a liquid at room temperature, so it was purified by distillation instead of sublimation. $^1$H NMR (benzene-$d_6$, ppm); 3.11 (s, 24, NCH$_3$), 2.15 (t, 8, J=8.0 Hz, CCH$_2$CH$_2$CH$_3$), 1.49 (m, 8, CCH$_2$CH$_2$CH$_3$), 0.90 (t, 12, J=6.8 Hz, CCH$_2$CH$_2$CH$_3$). $^{13}$C NMR (benzene-$d_6$, ppm); 179.27 (s, CCH$_2$CH$_2$CH$_3$), 34.28 (s, NCH$_3$), 26.14 (s, CCH$_2$CH$_2$CH$_3$), 19.82 (s, CCH$_2$CH$_2$CH$_3$), 14.47 (s, CCH$_2$CH$_2$CH$_3$).

Anal. Calcd. for C$_{24}$H$_{52}$N$_8$Zr: C, 52.99; H, 9.63; N, 20.60. Found: 53.63; H, 9.87; N, 20.89. Its T$_{1/2}$ value is 246° C. and it evaporates leaving a negligible residue.

Example 10

Synthesis of tetrakis(N,N'-dimethylbutyramidinato) hafnium(IV)

This compound was prepared from HfCl$_4$ by the salt metathesis reaction described in Example 9. It may also be prepared by a ligand exchange reaction similar to the one described in Example 1. The compound is a liquid at room temperature, so it was purified by distillation instead of sublimation. $^1$H NMR (benzene-$d_6$, ppm): 3.15 (s, 24, NCH$_3$), 2.13 (t, 8, J=8.0 Hz, CCH$_2$CH$_2$CH$_3$), 1.49 (m, 8, CCH$_2$CH$_2$CH$_3$), 0.89 (t, 12, J=6.8 Hz, CCH$_2$CH$_2$CH$_3$). $^{13}$C NMR (benzene-$d_6$, ppm): 178.87 (s, CCH$_2$CH$_2$CH$_3$), 34.08 (s, NCH$_3$), 26.29 (s, CCH$_2$CH$_2$CH$_3$), 19.82 (s, CCH$_2$CH$_2$CH$_3$), 14.41 (s, CCH$_2$CH$_2$CH$_3$). Anal. Calcd. for C$_{24}$H$_{52}$HfN$_8$: C, 45.67; H, 8.30; N, 17.75. Found: 45.31; H, 8.81; N, 17.61. Its T$_{1/2}$ value is 252° C. and it evaporates leaving a negligible residue.

Example 11

Synthesis of tetrakis(N,N'-diethylacetamidinato) zirconium(IV)

A dioxane solution of lithium N,N'-diethylacetamidinate was prepared by the method described in Example 4, using ethylamine in place of methylamine. This solution was then used with ZrCl$_4$ in the salt metathesis method described in Example 5 to prepare tetrakis(N,N'-diethylacetamidinato)zirconium(IV). It may also be prepared by a ligand exchange reaction similar to the one described in Example 1. $^1$H NMR (benzene-$d_6$, ppm)-3.32 (q, 16, J=7.2 Hz, NCH$_2$CH$_3$), 1.63 (s, 12, CCH$_3$), 1.10 (t, 24, J=7.2 Hz, NCH$_2$CH$_3$). $^{13}$C NMR (benzene-$d_6$, ppm); 173.59 (s, CCH$_3$), 41.38 (s, NCH$_2$CH$_3$), 18.00 (s, NCH$_2$CH$_3$), 10.20 (s, CCH$_3$). Anal. Calcd. for C$_{24}$H$_{52}$N$_8$Zr: C, 52.99; H, 9.63; N, 20.60. Found: 52.86; H, 9.40; N, 20.99. Its T$_{1/2}$ value is 242° C. and it evaporates leaving a negligible residue.

Example 12

Synthesis of tetrakis(N,N'-diethylacetamidinato) hafnium(IV)

This compound was prepared from HfCl$_4$ by the salt metathesis method described in Example 11. It may also be prepared by a ligand exchange reaction similar to the one described in Example 1. $^1$H NMR (benzene-$d_6$, ppm): 3.32 (q, 16, J=7.2 Hz, NCH$_2$CH$_3$), 1.63 (s, 12, CCH$_3$), 1.10 (t, 24, J=7.2 Hz, NCH$_2$CH$_3$). $^{13}$C NMR (benzene-$d_6$, ppm): 173.07 (s, CCH$_3$), 41.08 (s, NCH$_2$CH$_3$), 18.00 (s, NCH$_2$CH$_3$), 10.59 (s, CCH$_3$). Anal. Calcd. for C$_{24}$H$_{52}$N$_8$Hf: C, 45.67; H, 8.30; N, 17.75. Found: 46.17; H, 7.93; N, 17.27. Its T$_{1/2}$ value is 264° C. and it evaporates leaving a negligible residue.

Example 13

Synthesis of tetrakis(N,N'-diethylacetamidinato) tantalum(IV)

This compound was prepared in two steps from tantalum pentachloride. The first step involved the addition under nitrogen at −78° C. of an ether solution of tantalum pentachloride (0.95 mmol, 331 mg in 20 mL ether) to a solution of lithium N,N'-diethylacetamidinate (2 mmol in 20 mL ether, prepared in situ from the amidine and a hexanes solution (2.6 M) of n-butyl lithium). The intermediate, tentatively described as trischloro-bis(N,N'-diethylacetamidinato)tantalum(V) was partially soluble in ether, giving an orange solution. Some dioxane was added to help dissolve the intermediate, and two more equivalents of lithium N,N'-diethylacetamidinate (2 mmol in 20 mL ether, prepared in situ from the amidine and a hexanes solution (2.6 M) of n-butyl lithium) were added at room temperature. One equivalent of sodium amalgam was also added (22.8 mg, in a mercury amalgam having 0.645% sodium by weight, 3.53 g). The solution was stirred overnight at room temperature. The solution turned dark purple within 12 hours. The ether was stripped under vacuum, and pentane (20 mL) was added. The purple solution was decanted and separated from the mercury and the insoluble materials. It was dried under vacuum and yielded the product, a purple solid, which can tentatively be described as tetrakis(N,N'-diethylacetamidinato)tantalum (IV). The product could be sublimed under vacuum, and the sublimed fraction could also be sublimed again without decomposition at 150° C. at a pressure of 0.01 mmHg.

Although the product contained impurities, its color and the fact it could be sublimed under vacuum with no decomposition indicate it is likely to be a volatile tantalum(IV) amidinate.

Example 14

Synthesis of other metal(IV) tetra-amidinates

Compounds containing other metal centers can be prepared in ways similar to those described in Example 3, by using a suitable metal source in place of $ZrCl_4$. For example, tetrakis(N,N'-dimethylacetamidinato) tungsten(IV) is prepared using tungsten(IV) chloride, $WCl_4$; tetrakis(N,N'-dimethylacetamidinato)tin(IV) is prepared using tin(IV) chloride, $SnCl_4$; tetrakis(N,N'-dimethylacetamidinato)tellurium (IV) is prepared from $TeCl_4$; and tetrakis(N,N'-dimethylacetamidinato)uranium(IV) is prepared in using uranium(IV) chloride, $UCl_4$.

Example 15

Atomic layer deposition of hafnium oxide from tetrakis(N,N'-dimethylbutyramidinato)hafnium(IV) and ozone 10 mmol cm$^{-2}$ doses of the vapor of tetrakis(N,N'-dimethylpropionamidinato)hafnium(IV) from a direct liquid injection system at 200° C. are introduced with an exposure of 10 Torr-sec in to an ALD reactor at 400° C., alternately with 20 nmol cm$^{-2}$ doses of ozone at an exposure of 10 Torr-sec. A film of hafnium oxide is deposited conformally inside narrow holes with high aspect ratio of 80:1.

Example 16

Atomic Layer Deposition of hafnium oxide from tetrakis(N,N'-dimethylbutyramidinato)hafnium(IV) and water vapor 10 nmol cm$^{-2}$ doses of the vapor of tetrakis(N,N'-dimethylpropionamidinato)hafnium(IV) from a direct liquid injection system at 200° C. are introduced with an exposure of 10 Torr-sec in to an ALD reactor at 400° C., alternately with 20 nmol cm$^{-2}$ doses of water vapor at an exposure of 10 Torr-sec. A film of hafnium oxide is deposited conformally inside narrow holes with high aspect ratio of 80:1.

Example 17

Atomic layer deposition of hafnium nitride from tetrakis(N,N'-dimethylbutyramidinato)hafnium(IV) and ammonia 10 nmol cm$^{-2}$ doses of the vapor of tetrakis(N,N'-dimethylpropionamidinato)hafnium(IV) from a direct liquid injection system at 200° C. are introduced with an exposure of 10 Torr-sec in to an ALD reactor at 400° C., alternately with 20 nmol cm$^{-2}$ doses of ammonia at an exposure of 10 Torr-sec. A film of hafnium nitride is deposited conformally inside narrow holes with high aspect ratio of 80:1.

Other variations on the synthetic methods and other metal (IV) amidinate compounds will be apparent to those of skill in the art.

What is claimed is:

1. A compound having the structural formula

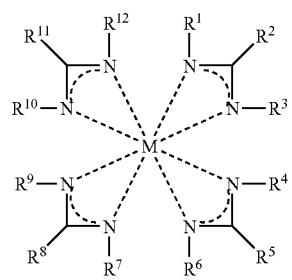

in which M is a metal in the +4 oxidation state and each of $R^1$ through $R^{12}$ are independently selected from the group consisting of hydrogen, hydrocarbon groups, substituted hydrocarbon groups, and other groups comprising non-metallic atoms.

2. The compound of claim 1, wherein the hydrocarbon group is selected from the group consisting of alkyl, cycloalkyl, alkenyl, cycloalkenyl, alkynyl and cycloalkynyl groups and the substituted hydrocarbon group consisting of fluoride derivatives of hydrocarbons.

3. The compound of claim 1, wherein the group comprising non-metallic atoms are selected from the group consisting of alkylsilyl and alkyl amino groups.

4. The compound of claim 1, wherein metal M is selected from the group consisting of zirconium, hafnium, tin, tantalum, niobium, tungsten, molybdenum, uranium, rhenium, platinum, osmium, iridium, ruthenium, palladium, titanium, rhodium, vanadium, cerium and lead.

5. The compound of claim 1, in which the metal M is selected from the group consisting of hafnium, zirconium, tantalum, niobium, tungsten, molybdenum, tin, tellurium and uranium.

6. The compound of claim 1, in which the metal M is zirconium.

7. The compound of claim 1, in which the metal M is hafnium.

8. The compound of claim 1, wherein at least one of $R^1$ through $R^{12}$ is a lower alkyl having 5 or less carbons.

9. The compound of claim 1, wherein $R^1$ through $R^{12}$ is selected from the group consisting of lower alkyls having 5 or less carbons and hydrogen.

10. The compound of claim 1, wherein $R^1$, $R^3$, $R^4$, $R^6$, $R^7$, $R^9$, $R^{10}$ and $R^{12}$ are alkyl groups that are un-branched at the α-position.

11. A process for forming a thin film comprising a metal, comprising:
exposing a heated surface to a vapor of one or more volatile compounds of claim 1.

12. The process of claim 11, wherein the hydrocarbon group is selected from the group consisting of alkyl, cycloalkyl, alkenyl, cycloalkenyl, alkynyl and cycloalkynyl groups and fluoride derivatives thereof.

13. The process of claim 11, wherein the group comprising non-metallic atoms are selected from the group consisting of alkylsilyl and alkyl amino groups.

14. The process of claim 11, wherein the metal M is selected from the group consisting of zirconium, hafnium, tin, tantalum, niobium, tungsten, molybdenum, uranium, rhenium, platinum, osmium, iridium, ruthenium, palladium, titanium, rhodium, vanadium, cerium, tellurium and lead.

15. The process of claim 11, wherein the metal M is selected from the group consisting of hafnium, zirconium, tantalum, niobium, tungsten, molybdenum, tin, tellurium and uranium.

16. The process of claim 11, wherein the metal M is zirconium.

17. The process of claim 11, wherein the metal M is hafnium.

18. The process of claim 11, wherein at least one of $R^1$ through $R^{12}$ is a lower alkyl having 5 or less carbons.

19. The process of claim 11, wherein $R^1$ through $R^{12}$ is selected from the group consisting of lower alkyls having 5 or less carbons and hydrogen.

20. The process of claim 11, in which the substrate is also exposed to a source of oxygen, and the thin film comprises a metal oxide.

21. The process of claim 20, in which the source of oxygen comprises water vapor.

22. The process of claim 20, in which the source of oxygen comprises dioxygen.

23. The process of claim 20, in which the source of oxygen comprises ozone.

24. The process of claim 11, in which the substrate is also exposed to a source of nitrogen, and the thin film comprises a metal nitride.

25. The process of claim 24, in which the source of nitrogen comprises ammonia.

26. The process of claim 11, wherein the film is deposited in a CVD process.

27. The process of claim 11, wherein the film is deposited in an ALD process.

28. The process of claim 11, wherein the vapor is obtained by vaporizing a solid form of the compound.

29. The process of claim 11, wherein the vapor is obtained by vaporizing a liquid form of the compound.

30. The process of claim 11, wherein the vapor is obtained by vaporizing the compound at a temperature in the range of 100 to 250° C.

31. The process of claim 11, wherein the surface is at a temperature in the range of about 200 to 500° C.

* * * * *

UNITED STATES PATENT AND TRADEMARK OFFICE
CERTIFICATE OF CORRECTION

PATENT NO. : 7,638,645 B2 Page 1 of 1
APPLICATION NO. : 11/581987
DATED : December 29, 2009
INVENTOR(S) : Gordon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 629 days.

Signed and Sealed this

Twenty-first Day of December, 2010

David J. Kappos
*Director of the United States Patent and Trademark Office*